United States Patent [19]

Stitt

[11] 3,961,078

[45] June 1, 1976

[54] SOLUBLE WASTE CONVERSION PROCESS AND PASTEURIZED PROTEINACEOUS PRODUCTS

[76] Inventor: Paul A. Stitt, 1318 S. Eighth St., Manitowoc, Wis. 54220

[22] Filed: Mar. 21, 1975

[21] Appl. No.: 560,748

Related U.S. Application Data

[63] Continuation of Ser. No. 326,228, Jan. 24, 1973, abandoned.

[52] U.S. Cl. .................................. 426/41; 426/53; 210/11; 210/15; 426/43
[51] Int. Cl.² ..................... A23C 5/00; A23K 1/08; A23J 1/20; C02C 1/02
[58] Field of Search ................................. 426/41–43, 426/46, 52, 53; 210/11, 15; 195/96

[56] References Cited
UNITED STATES PATENTS

| | | | |
|---|---|---|---|
| 2,809,113 | 10/1957 | Stimpson et al. | 426/41 |
| 3,410,755 | 11/1968 | Etchells et al. | 195/96 |
| 3,462,275 | 8/1969 | Bellamy | 426/53 |
| 3,546,071 | 12/1970 | Douros et al. | 195/96 X |
| 3,642,580 | 2/1972 | Ghose | 195/33 |
| 3,753,725 | 8/1973 | Williams et al. | 195/31 R |
| 3,838,198 | 9/1974 | Bellamy et al. | 426/53 |

*Primary Examiner*—Lionel M. Shapiro
*Attorney, Agent, or Firm*—Sughrue, Rothwell, Mion, Zinn & Macpeak

[57] ABSTRACT

A process for treating soluble biodegradable organic waste material which comprises:
a. preparing a reaction mixture of soluble biodegradable organic waste material and a thermophilic aerobic microorganism culture capable of digesting such soluble material and containing soluble sources of manganese, magnesium, phosphorus, iron and nitrogen in a liquid medium and at a pH ranging from about 5.5 to 9, the soluble organic material content being in excess of 1 gram per liter,
b. introducing oxygen into the mixture so as to maintain the dissolved oxygen content at least 0.01 mg per liter of said mixture while
c. maintaining said mixture at a temperature of from 45° to 70°C for a time sufficient to convert the organic waste material into cellular proteinaceous material, and
d. separating the cellular proteinaceous material produced.

18 Claims, 1 Drawing Figure

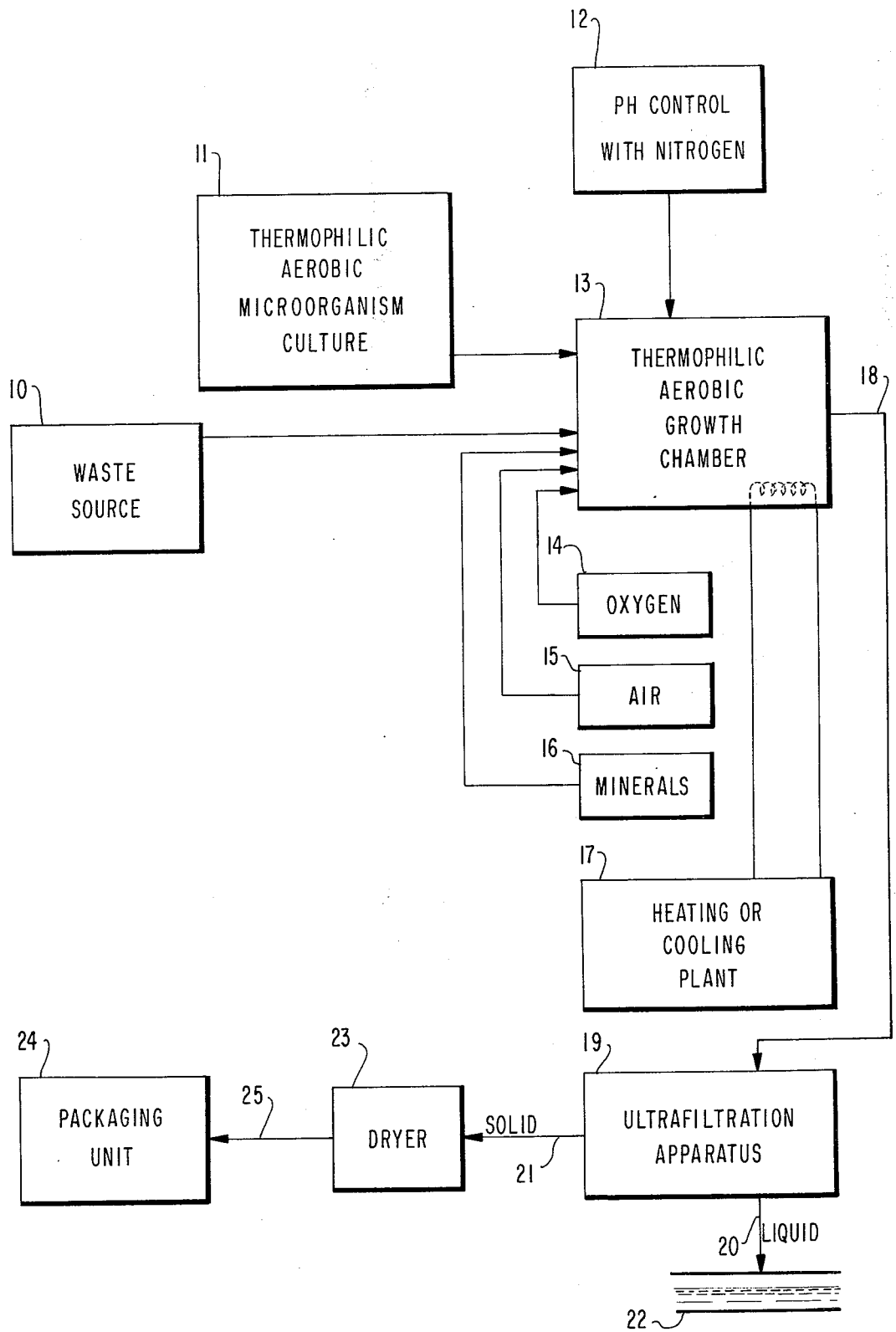

SOLUBLE WASTE CONVERSION PROCESS AND PASTEURIZED PROTEINACEOUS PRODUCTS

This is a continuation of application Ser. No. 326,228, filed Jan. 24, 1973, now abandoned.

BACKGROUND OF THE INVENTION

1. Field of the Invention

The present invention relates to a process for conversion of soluble biodegradable organic compounds into useful products. The process of the invention converts such soluble biodegradable organic compounds into useful products, such as, high protein concentrates for animal fodder and sources of protein, enzymes and vitamins. The process of the invention can be used for treating certain food processing wastes and for treating certain industrial wastes.

2. Description of the Prior Art

Municipal sewage generally contains about 100 to 300 mg/l solubles and about 100 to 500 mg/l solids and the treatment in a municipal sewage plant is to break down and remove both solubles and solids. The predominant problem, however, with municipal sewage treatment is to remove the solids and since the amount of solubles present in material to be treated generally is minor, there is little concern with the solubles present. In contrast, biodegradable industrial wastes generally contain about 1000 to 100,000 mg/l. For example, cheese whey has a solubles content of about 60,000 mg/l and only a trace of solids.

Industrial wastes in this form cause extreme problems and upsets to sewage treatment plants because of the high concentration of waste and as a result of the high level, the material must either be treated prior to treatment by municipal sewage treatment plants or disposed of using alternative methods. Conventional treatment of industrial wastes is dilution with water and then to treat the diluted wastes in the same manner as municipal sewage or simply disposal by injecting of the waste into deep wells. These wastes are not, therefore, recovered.

Present day conventional methods for treatment of municipal sewage wastes generally containing a large solids content and minor amounts of solubles on a relative basis are based upon subjecting the wastes to microbial oxidation by the activated sludge process. Activated sludge and flocculated waste generally has a solids content of about 200,000 mg/l and in the activated sludge process used to treat such wastes up to 90% of the organic material is removed as a solid residue or a semi-solid sludge. The sludge and flocculated wastes are stabilized in an anaerobic digester for about 30 days. The waste then must be disposed of by such methods as use as land fillings, disposal at sea, incineration, further treatment to produce fertilizers, and use in soil conditioning, etc. Where the product is to be used as a land fill, additional problems arise due to the presence of pathogenic organisms and generally thermophilic conditions are employed in the digester to destroy pathogenic bacteria. Due to environmental concerns of space limitations, of odors and air quality, of problems with pathogenicity, the above methods of disposal are expensive and environmentally of concern. Therefore, at the present time, there is great interest and activity in research on waste treatment methods.

For example, U.S. Pat. No. 3,462,275 discloses a process in which solid, organic biodegradable wastes such as solid sludge from primary sewage treatment plants, activated sludge from secondary sewage treatment plants, and solid wastes obtained by coagulation or flocculation of dilute aqueous waste containing suspensions, i.e., coagulation or flocculation is used since the solid materials have about the same specific gravity as the medium and do not settle, are treated with mixed populations of selected thermophilic microorganisms under aerobic conditions at temperatures of from 45° to 80°C. Cellular proteinaceous materials and other cellular products are disclosed as being produced by the above-described process. The emphasis in this process is the treatment of solid waste materials, i.e., sewage sludge, activated sludge, animal wastes containing about 20% by weight solids with low solubles levels or the concentration by flocculation of dilute suspensions of solid wastes and the utilization of organisms and conditions which promote the breakdown or organic polymers such as cellulose materials, the fungi present in such a mixed population being so favored and producing cellular proteinaceous material and products which, due to their nature, are useful as feeds only for ruminants or must be further processed for ready availability by other animals by extraction of the crude proteins with hot alkali followed by purification.

The above-described process is not and the prior art in general has not been concerned with the problems of soluble biodegradable organic waste materials present, for example, in food processing wastes, e.g., various types of cheese whey, and in industrial waste solutions such as those generated in the petroleum and photographic industries, these materials comprising generally soluble organic waste materials. These materials generally contain soluble wastes dissolved in solution and at concentrations which are sufficiently high to cause environmental problems if discharged directly into the biosphere and generally cause severe treatment problems if not pretreated, e.g., by dilution with water, if fed directly to solid waste treatment plants.

It is an object of this invention to provide a waste treatment method for disposing of food processing wastes and industrial biodegradable wastes.

It is also an object of this invention to provide a process for producing proteins, vitamins, enzymes and unidentified growth factors from sources of soluble biodegradable waste materials.

It is additionally an object of this invention to provide a process for producing proteins from such soluble wastes in a high yield.

It is another object of this invention to provide a process for producing a source of proteins as animal feeds and feed supplements which can be readily utilized and metabolized by a wide variety of animals without the need for further significant treatment or processing.

It is a further object of this invention to provide a method of producing from soluble biodegradable waste materials an effluent low in biochemical oxygen demand, low in nitrogen, and low in phosphorus which meets present Federal Environmental Water Quality Standards in most locations and can be discharged directly into rivers and streams without causing pollution problems or which can be discharged through conventional municipal sewage systems without providing an unreasonable load to such sewage systems.

These and other objects of the invention are obtained in the practice of the process of this invention as hereinafter described.

SUMMARY OF THE INVENTION

The process of this invention comprises treating soluble biodegradable organic waste materials in a liquid medium with selected thermophilic microorganisms, as hereinafter described, and holding the mixture at temperatures of from about 45°C to 70°C while supplying oxygen and required nitrogen and trace minerals to the mixture for a time sufficient for conversion of the soluble organic wastes. Within this temperature range, under these aerobic conditions and in the presence of the added nitrogen and minerals the thermophilic microorganisms multiply and convert the soluble organic waste materials to cellular proteinaceous materials and other cellular products.

BRIEF DESCRIPTION OF THE ACCOMPANYING DRAWING

The accompanying drawing is a flowsheet illustrating an embodiment of the process of this invention.

DETAILED DESCRIPTION OF THE INVENTION

The water-soluble organic biodegradable waste materials which can be treated in accordance with the process of this invention basically can include the waste materials from any process which gives rise to wastes containing water-soluble biodegradable materials, including fresh cheese whey, cottage cheese whey, deproteinated cheese whey, butter whey, vegetable processing wastes, brewery wastes, chemical processing wastes, soy bean processing wastes, sugar processing wastes, corn processing wastes, cellulose acetate processing wastes, photographic film developing wastes containing sources of carbon such as acetic acid, hydrocarbon refining wastes, and plastic manufacturing wastes.

The amount of soluble biodegradable organic waste materials utilized as a starting material in the process of this invention which can be present in the liquid medium is not critical and can be as low as about 1 gram per liter to as high as about 100 grams per liter or higher. Use of less than 1 gram per liter is not desired from an economic standpoint and it is especially preferred for economic reasons to employ a biodegradable mixture which contains at least 10 grams per liter of biodegradable organic material since employing waste materials which contain greater than 990 grams per liter of water requires the heating of excessive amounts of water without any commensurate advantages. Use of amounts substantially higher than 100 grams per liter, while possible, gives rise to processing problems such as high oxygen transfer demand.

Oxygen is necessary in the process of this invention, and any conventionally known technique for supplying oxygen into a substantially liquid system can be employed. For example, oxygen or an oxygen containing gas such as air can be supplied under normal or superatmospheric pressures by bubbling the oxygen or air into the reaction mixture containing the thermophilic microorganisms, the soluble biodegradable organic waste materials and the necessary nitrogen and trace minerals and agitating the reaction mixture. While the amount of oxygen added generally will be dependent upon the amount of soluble biodegradable organic waste materials present it is desirable that the mixture contains at least 0.01 mg of oxygen per liter of the mixture. The amount of dissolved oxygen can be as high as 4 mg per liter of mixture or higher, for example, up to the oxygen saturation point. The upper limit on the amount of oxygen present is merely an economical consideration. Large amounts of oxygen can be utilized but give no economical advantage in the process of this invention.

In the practice of this invention, trace elements must be present with the thermophilic microorganisms to favor the growth of the thermophilic microorganisms and, thereby, the efficient conversion of the soluble organic biodegradable wastes in accordance with this invention. Generally a wide variety of trace elements are present inherently in waste materials but even when these trace elements are present they usually are not present at a high enough level for sustaining the efficient propagation of thermophilic bacteria and to obtain high yields. Generally, for propagation of bacteria elements such as manganese, iron, phosphorus, magnesium and nitrogen are required. In this invention manganese must be present in the mixture to an extent of at least one part by weight to 50 parts by weight of 10,000 parts by weight of carbon in the waste source. Any soluble salt containing manganese, such as manganese sulfate, manganese acetate, and manganese chloride, can be utilized to provide the manganese required. Iron must be present in the mixture to an extent of at least one part by weight to 50 parts by weight of iron to 10,000 parts by weight of carbon in the waste source. Any soluble salt containing iron, such as ferrous sulfate, ferric chloride and ferrous acetate can be used. Ferrous sulfate is the preferred iron source. Phosphorus also must be present in the mixture to an extent of at least one part by weight to 5 parts by weight of phosphorous to 100 parts by weight of carbon in the waste source. Any soluble material containing phosphorous, such as potassium phosphate, sodium phosphate, magnesium phosphate and phosphoric acid, can be used. Potassium phosphate is the preferred phosphorus source. Magnesium must be present in the mixture to an extent of at least one part by weight to 10 parts by weight of magnesium to 1,000 parts by weight of carbon in the waste source. Any soluble salt containing magnesium, such as magnesium sulfate, magnesium chloride and magnesium acetate, is suitable. Magnesium sulfate is preferred. Nitrogen must be present in the mixture to an extent of at least one part by weight of 6 parts by weight of nitrogen to 50 parts by weight of carbon. Any soluble nitrogen containing compound such as ammonia, urea, nitric acid, ammonium sulfate and ammonium phosphate can be suitably employed. Ammonia is the preferred source of nitrogen.

It is also possible, where desired, to utilize the same source material for two of the above required trace elements. For example, magnesium phosphate could be used to provide simultaneously both the source of magnesium and phosphorus. In view of the differing ranges set forth above, where a common source material is used it may be necessary to additionally achieve the level of the element required in a higher amount. For example, since magnesium should be present at a lower level than the phosphorous where magnesium phosphate is used, it may be necessary to use an additional source of phosphorus to achieve the phosphorus content range set forth above.

It should be emphasized with respect to the above set forth trace elements that the process of this invention is, as described above, applicable to a broad range of different types of soluble biodegradable organic wastes. These wastes will, of course, vary in their chemical constitution and even within the same type of waste material the chemical constitution may fluctuate, in the case of food processing wastes due to their natural product nature or in the case of industrial wastes due to changes in the processing conditions employed in the processes which produce them. Thus, with respect to the above set forth ranges for the trace elements and nitrogen which are employed in the process of this invention, depending upon the chemical constitution of the organic waste material it may not be necessary affirmatively to add the magnesium, the iron, the manganese or the phosphorus, if sufficient levels are present inherently in the raw waste material such that the reaction mixture prepared for subjecting to the process of this invention contains the above set forth materials in the prescribed ranges.

Other minerals can be added as is well known and customary in the art for mesophilic bacteria.

As has been pointed out above, the temperature at which process of this invention is operated can range from about 45° to 70°c. However, for best results, it is preferred to employ temperatures of from about 55° to 60°C. In this temperature range, the thermophilic microorganisms multiply rapidly in the presence of oxygen and in addition, where temperatures in excess of about 55°C are used, cellular proteinaceous materials and other cellular components produced are simultaneously pasteurized; that is, the pathogenic organisms, etc., which may be present in the waste material utilized are destroyed at these temperatures, thereby yielding a solid product which can be further employed as feed for animals or as feed supplements for animals without introducing pathogenic organisms into the animals. Temperatures outside the above ranges set forth are not conducive to the growth of the thermophilic organisms and the conversion of the waste material.

In the practice of this process, it is advantageous to control the pH of the system. The pH of the system should be maintained between about 5.5 and 9. It is preferred that the pH of the reaction mixture be maintained at approximately 6–8. The addition of ammonia or another nitrogen source can be utilized where desired to achieve pH control within this above set forth range. The pH range, above described, favors the growth of the thermophilic microorganisms and thereby promotes a more efficient conversion of the soluble organic biodegradable waste material.

In the practice of this invention, a mixed culture of thermophilic aerobic microorganisms is used and this mixed culture of thermophilic aerobic microorganisms can be obtained, for example, from a compost heap, baby foods, pasteurized milk, the rumen of a cow, etc. A preferred culture source is pasteurized milk. The microorganisms adapt to the carbonaceous material in the waste source. Under the controlled conditions described above, the microorganisms thrive and multiply rapidly and digest the soluble organic biodegradable waste to yield cellular proteinaceous and other cellular materials, and at the same time, if temperatures in excess of 55°C are employed, any pathogenic organisms are destroyed and a pasteurized proteinaceous product is produced. After the process is initiated, it may be advantageous to heat or cool the reaction mixture to regulate the temperature in order to hold the temperature within the range above described which is conducive to the microbiological activity occurring. When the microorganisms have consumed most of the biodegradable material, additional waste material, trace elements, etc., can be added and the process continued. The waste source can be added on a continuous basis and the spent material can be removed on a continuous basis. Thus, the process can be conducted on a batch basis, a semi-continuous basis or a continuous basis. The average residence time of the waste source in conducting the process of this invention can range from about 1 to 20 hours. A preferred average residence time is from about 2 to 10 hours.

The populations of thermophilic microorganisms that are employed in the process of this invention are selected in order that soluble organic biodegradable wastes such as the sugars, alcohols, organic acids, fatty acids, fats, amino acids and proteins, etc., can be converted at practical rates. The mixed populations of thermophilic microorganisms useful in the process of this invention include any or all of the following: *Bacillus stearothermophilus, Bacillus alimentophilus, Bacillus violaceous, Bacillus thermoindifferens*, other Bacillus species, *Lactobacillus bulgaricus, Lactobacillus thermophilus, Lactobacillus delbrueckii*, other *Lactobacillus species, Micrococcus thermophilus* and other *Micrococcus* species, Pseudomonas species, *Flavabacterium* species, etc.

While not desiring to be bound by theory, it is believed that the soluble organic source material being of a relatively low molecular weight, the processing conditions utilized and the addition of nitrogen and high levels of trace elements provide conditions favoring the growth of bacteria to the exclusion of other microorganisms such as fungi, the latter being favored, for example, by the organic source materials and processing conditions utilized in U.S. Pat. No. 3,462,275. This results in the product produced having differing characteristics. The fungal protein product produced in U.S. Pat. No. 3,462,275, while easily harvested, has the disadvantage in the difficult digestibility of the fungal product by non-ruminants and the low protein content of the product. In contrast to this, the process of this invention favors the growth of bacteria which, when subsequently recovered from the reaction mixture after conducting the process of this invention, provides a source of readily available proteins in high yield, the product being readily digestible, high in protein level and essentially utilizable in a wide variety of applications without any substantial additional processing. For example, the protein contained in the bacterial cells can be easily digested without any treatment such as extraction, but it may be desirable to heat the product to kill the bacteria where used directly. The protein contained in the product of the process of this invention is loosely contained in bacterial cell walls and the protein content of the product of this invention ranges from about 60 to 80% by weight. This loosely bound nature renders it readily available for use without additional processing. The protein produced in accordance with U.S. Pat. No. 3,462,275 is tightly bound within fungal cell walls which must be extracted and contains a protein content of only about 30 to 50% by weight. Yields generally obtainable using the process of this invention range from about 30 to 80, more generally about 50, parts by weight for each 100 parts by weight of soluble biodegradable organic waste material.

The mixed population is not limited to the above-mentioned microorganisms but includes other uncharacterized strains. Such a population includes organisms the growth of which will, as discussed above, not be favored, but also those organisms which cannot live in the mentioned substrates. These latter organisms may be beneficial in that they may contribute to the overall assimilation rate by producing growth factors for the active organisms.

At the end of the process, the reacted waste mixture can be processed by separation of solids and liquids, as for example, by ultrafiltration, for the recovery of the cellular proteinaceous materials and other cellular components produced. Centrifugation can be used but it is not desired because of the expense. Drying of the reaction mixture also can be used as a method of recovery but has the disadvantage of the possibility of thermal degradation of the protein product and the pressure of high salt levels in the product. Ultrafiltration of the bacterial cells is preferred as a recovery method. The liquid separated is sufficiently pure that in most locations it may be passed to a river or a stream or processed through a municipal sewage system, alternatively.

With the process of this invention, about 80 to 95% of the soluble biodegradable organic waste material is removed.

The progress of the process of this invention can be followed using conventional techniques. The static and dynamic dissolved oxygen level can be used to monitor the growth rate. Use of biological oxygen demand and chemical oxygen demand of the waste material before processing and after processing can be used to determine the level of pollutants removed. The yield of the bacteria can be determined by removal of the bacterial cells, e.g., using a 0.45 micron filter, drying and weighing. In a continuous process, the process usually is monitored continuously and the results evaluated after a steady state has been reached, e.g., after about 20 hours. The trace minerals added are added step-wise during continuous operation. In the batch process the reaction mixture is prepared and the reaction stops when the biological oxygen demand or chemical oxygen demand stops decreasing or meets an acceptable level. The liquid effluent separated from the solid cellular proteinaceous material can be analyzed using standard water analysis methods (as prescribed by the American Water Works Association) and if the phosphorus and nitrogen level, or the biochemical oxygen demand of the liquid is too high, it may be recycled for further processing in accordance with the process of this invention.

Turning now to the accompanying drawing, the accompanying drawing illustrates the flowsheet of an embodiment of the process of this invention. In greater detail, 13 represents a thermophilic aerobic growth chamber to which a waste source 10 containing soluble biodegradable organic materials, after pH measurement and adjustment, if necessary, is added. Trace minerals and elements 16 are added to the waste source and a source of oxygen, shown in the flowsheet by air source 15 and oxygen source 14 for easy maintenance of the dissolved oxygen level, is provided. The pH of the reaction medium in growth chamber 13 is adjusted by nitrogen source addition 12. The thermophilic aerobic growth chamber can be heated or cooled as necessary using heating or cooling means 17, for example, by heating coils or baffles. At the end of the process, the converted waste mixture is withdrawn through conduit 18 and passed to an ultrafiltration unit 19 whereby the liquid 20 can be either disposed of or recycled. The solid material (converted proteinaceous material) separated at 19 is passed through conduit 21 to dryer 23 where a major proportion of the water from the solid material is removed. The dried material is then passed via conduit 25 to a packaging unit 24.

The following examples of this invention are given for the purposes of illustrating the invention in greater detail and are not to be construed as limiting the scope of the invention.

EXAMPLE 1

A 1-liter sample of cheese whey was mixed with two liters of water containing 100 PPM ferrous sulfate, 100 PPM magnesium sulfate, and 100 PPM manganese sulfate. This mixture contained 1.2 g/l whey protein. The temperature was held at 57°C and the pH maintained at 7.2 by adding ammonia and the amount of dissolved oxygen in the mixture was maintained greater than 0.01 mg per liter of the mixture by sparging air and agitating. Ten ml of liquid from the rumen of a cow was added as inoculum. After 10 hours, the organic material in the cheese whey had been consumed by thermophilic aerobic microorganisms. At that time, material of the same composition as was present originally in the growth chamber was added on a continuous basis and spent material was removed at the same rate. After operating continuously for at least 48 hours, the liquid medium contained 8.1 g/l cellular material. The spent broth was collected and concentrated by ultrafiltration. The solid cellular material obtained by drying contained 78% by weight protein. In excess of 70% of the biochemical oxygen demand had been removed from the cheese whey. The fermentation process caused a 5-fold increase in the protein content of the whey. The solid cellular material was fed to a dog that relished it. Pigs and calves to which the solid cellular material was fed also thrived on it. Sufficient pasteurized and converted whey protein could be produced by the process to supply one-half the daily requirements of dairy calves as a milk replacer made from the waste whey.

EXAMPLE 2

An industrial waste involved in the chemical treatment of cellulose that contained low levels of methanol, formic acid and phenol and containing 30 grams per liter of acetic acid was mixed with the following salts (g/l m = grams per liter of mixture): $Na_2HPO_4$, 2.0 g/l m; $KH_2PO_4$, 0.3 g/l m; $MgSO_4.7H_2O$ ), 0.3 g/l m; $MnSO_4$, 0.10 g/l m; $FeSO_4$, 0.20 g/l m. The mixture was maintained at 55°C and a pH of 7.2 by the addition of ammonia and the dissolved oxygen was maintained at greater than 0.01 mg of oxygen per liter of mixture by sparging air and agitating. Ten grams of material from a compost heap were added to three liters of the above-described mixture. After 20 hours, the acetic acid methanol and formic acid had been consumed by the bacteria and addition of fresh waste containing trace minerals was started. The spent broth was removed at the same rate. After operating for 24 hours under steady state conditions, no phenol could be detected (less than 10 parts per billion). The solid biomass was harvested and found to contain 81% by weight protein and high levels of B vitamins. The reaction medium contained 9.3 g/l cellular material before harvesting. After harvesting the BOD of the supernatant material was 1100 PPM compared to 26,000 PPM for the waste material before subjecting to the process of this invention.

EXAMPLE 3

Wastes from processing carrots were mixed with the following salts (grams per liter of mixture): $KH_2PO_4$, 0.1 g/l m, $MnSO_4$, 0.05 g/l m, $FeSO_4 \cdot 7H_2O$, 0.05 g/l m. The mixture was maintained at 50°C and a pH of 7.2 by adding ammonia and the dissolved oxygen was maintained at greater than 0.1 mg oxygen per liter by sparging air and agitating. Three liters of this mixture was inocculated with 25 milliliters of pasteurized milk. After 6 hours, 90% of the biochemical oxygen demand was removed by the growing bacteria. The biomass contained high levels of vitamins and enzymes. No putrifying odors were noticed during the process.

While the invention has been described in detail and in terms of specific embodiments thereof, it will be apparent that various changes and modifications can be made therein by one skilled in the art without departing from the spirit and scope thereof.

What is claimed is:

1. A process for treating soluble biodegradable organic waste material which comprises:
   a. preparing a reaction mixture consisting essentially of soluble biodegradable organic waste material and a microorganism culture consisting of thermophilic aerobic bacteria capable of digesting such soluble material and containing soluble sources of manganese, magnesium, phosphorus, iron and nitrogen in a liquid medium at a pH ranging from about 5.5 to 9, the soluble organic material content being in excess of 1 gram per liter;
   b. introducing an oxygenating gas into the mixture so as to maintain the dissolved oxygen content at least 0.01 mg per liter of said mixture while
   c. maintaining said mixture at a temperature of from 45° to 70°C for a time sufficient to convert the organic waste material into cellular proteinaceous material, and
   d. separating the cellular proteinaceous material produced.

2. The process as claimed in claim 1, wherein said biodegradable organic waste material is cheese whey.

3. The process as claimed in claim 1, wherein the process is continuous and the average residence time ranges from about 1 to 20 hours.

4. The process as claimed in claim 1, wherein the amount of a nitrogen present in said mixture is sufficient to provide a weight ratio of nitrogen to carbon in said waste material of at least 1 to 50.

5. The process as claimed in claim 1, wherein the amount of phosphorus present in said mixture is sufficient to provide a weight ratio of a phosphorus to carbon in said waste material of at least 1 to 100.

6. The process as claimed in claim 1, wherein the amount of iron present in said mixture is sufficient to provide a weight ratio of iron to carbon in said waste material of at least 1 to 10,000.

7. The process as claimed in claim 1, wherein the amount of manganese present in said mixture is sufficient to provide a weight ratio of manganese to carbon in said waste material of at least 1 to 10,000.

8. The process as claimed in claim 1, wherein the amount of magnesium present in said mixture is sufficient to provide a weight ratio of magnesium to carbon in said waste material of at least 1 to 5,000.

9. The process as claimed in claim 1, wherein said separating is by ultrafiltration.

10. The process as claimed in claim 1, wherein said temperature ranges from 55° to 70°C.

11. The process as claimed in claim 10, wherein the amount of a nitrogen present in said mixture is sufficient to provide a weight ratio of nitrogen to carbon in said waste material of at least 1 to 50.

12. The process as claimed in claim 10, wherein the amount of phosphorus present in said mixture is sufficient to provide a weight ratio of a phosphorus to carbon in said waste material of at least 1 to 100.

13. The process as claimed in claim 10, wherein the amount of iron present in said mixture is sufficient to provide a weight ratio of iron to carbon in said waste material of at least 1 to 10,000.

14. The process as claimed in claim 10, wherein the amount of manganese present in said mixture is sufficient to provide a weight ratio of manganese to carbon in said waste material of at least 1 to 10,000.

15. The process as claimed in claim 10, wherein the amount of magnesium present in said mixture is sufficient to provide a weight ratio of magnesium to carbon in said waste material of at least 1 to 5,000.

16. The process as claimed in claim 10, wherein said separating is by ultrafiltration.

17. The process of claim 1, wherein said thermophilic bacteria is a *Bacillus* species, a *Lactobacillus* species, a *Micrococcus* species, a *Pseudomonas* species or a *Flavabacterium* species.

18. The process of claim 17, wherein the bacteria is selected from a class consisting of *Bacillus stearothermophilus*, *Bacillus alimentophilus*, *Bacillus violaceous*, *Bacillus thermoindifferens*, *Lactobacillus bulgaricus*, *Lactobacillus thermophilus*, *Lactobacillus delbrueckii* and *Micrococcus thermophilus*.

* * * * *